(12) United States Patent
Beck (10) Patent No.: US 6,731,977 B2
(45) Date of Patent: May 4, 2004

(54) IONTOPHORETIC ELECTRODE WITH IMPROVED CURRENT DISTRIBUTION

(75) Inventor: Jon E. Beck, Salt Lake City, UT (US)

(73) Assignee: IOMED, Inc., Salt Lake City, UT (US)

( * ) Notice: Subject to any disclaimer, the term of this patent is extended or adjusted under 35 U.S.C. 154(b) by 0 days.

(21) Appl. No.: 09/766,767

(22) Filed: Jan. 22, 2001

(65) Prior Publication Data

US 2002/0099320 A1 Jul. 25, 2002

(51) Int. Cl.[7] ................................................. A61N 1/30
(52) U.S. Cl. ........................................ 604/20; 607/115
(58) Field of Search ............................ 604/20; 607/152, 607/115; 600/372

(56) References Cited

U.S. PATENT DOCUMENTS

| | | | | |
|---|---|---|---|---|
| 4,744,787 A | * | 5/1988 | Phipps et al. ................. 604/20 |
| 5,002,527 A | * | 3/1991 | Reller et al. |
| 5,053,001 A | * | 10/1991 | Reller et al. |
| 5,057,072 A | * | 10/1991 | Phipps ........................ 424/449 |
| 5,320,731 A | * | 6/1994 | Muller et al. |
| 5,573,503 A | * | 11/1996 | Untereker et al. |
| 5,792,097 A | * | 8/1998 | Reddy |
| 5,848,985 A | * | 12/1998 | Muroki |

FOREIGN PATENT DOCUMENTS

GB 2239803 * 7/1991

* cited by examiner

*Primary Examiner*—Mark Bockelman
(74) *Attorney, Agent, or Firm*—Factor & Lake (57) ABSTRACT

An electrode for use in an iontophoretic drug delivery having a substantially uniform distribution of current about the electrode. One such electrode includes a substrate, at least one first conductive layer of material disposed upon the substrate and at least one dielectric layer of material disposed upon at least a portion of the at least one conductive layer of material. The dielectric layer cooperates with the conductive layer of material to promote the substantially uniform distribution of current. Another such electrode includes a substrate, a conductive layer of material and a sacrificial layer of material.

26 Claims, 5 Drawing Sheets

IONTOPHORETIC ELECTRODE WITH IMPROVED CURRENT DISTRIBUTION

BACKGROUND OF THE INVENTION

1. Field of the Invention

The present invention is directed to iontophoretic drug delivery systems, and more particularly to electrodes having improved current distribution for iontophoretic drug delivery.

2. Background Art

The use of iontophoretic drug delivery systems has been known in the art for several years. Such devices are generally used to deliver a drug to a patient through the patient's skin or through the patient's eye. Generally, such devices comprise an electrode assembly (having a negative and positive electrode) and a power source/control module which is attached to the electrode assembly. The power source provides a potential difference between the electrodes, which facilitates the ionization of materials and the delivery of medicament into a patient.

Figure 10:
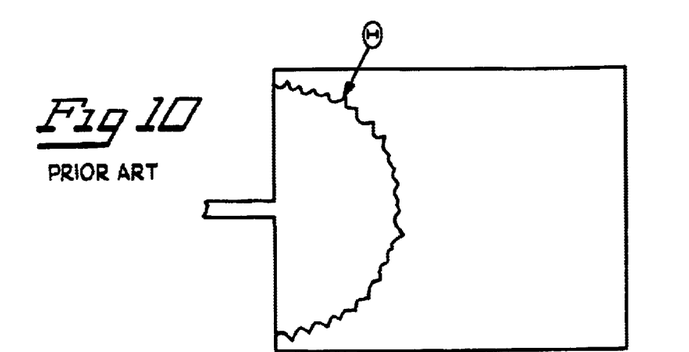
FIG. 10 of the drawings is a schematic partial top plan view of a prior art positive electrode assembly, showing in particular the current distribution across the surface of the electrode.

One problem that has been encountered with the electrode assembly is that the electric current has not been spread uniformly across the electrode. In particular, with respect to conventional positive electrodes, as shown in FIG. 10 (prior art), there is a tendency of the electric current (Θ) to refrain from spreading across the electrode; instead, the electric current is concentrated around the electrode lead (or the input of the electrical current). As such, the ionic reaction in which the electrode participates, occurs only in the regions proximate the lead, and does not reach much of the electrode. In turn, as the electrode region proximate the lead is sacrificed in the reaction, eventually, the region around the lead is fully depleted, and the reaction ceases. Often the reaction ceases because the region around the lead is depleted even though much of the electrode remains operable if the electric current from the lead could extend to those regions of the electrode.

Figure 18:
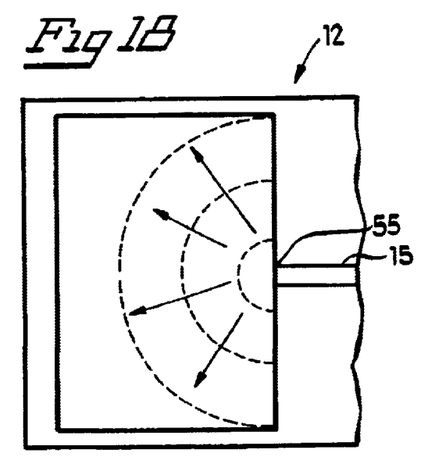
FIG. 18 of the drawings is a schematic partial top plan view of a prior art negative electrode assembly, showing in particular the current distribution across the surface of the electrode.

A similar problem can be seen relative to negative electrodes. In particular, as shown in FIG. 18 (prior art), with a conventional electrode, the current (θ) is concentrated proximate the electrical lead. As the reaction progresses and only after the negative electrode reacts for a period of time, the reaction spreads as a frontier across the electrode. Over time, the entire electrode is utilized, however it is not uniformly utilized, which leads to current concentrations in portions of the electrode.

Accordingly, it is an object to provide an electrode having a current distribution element which provides improved distribution of current about an electrode.

SUMMARY OF THE INVENTION

The invention comprises an electrode for use in an iontophoretic drug delivery apparatus. The electrode comprises at least one first conductive layer of material and at least one dielectric layer of material disposed upon at least a portion of, but less than the entirety of, the at least one conductive layer of material.

In a preferred embodiment, the electrode further comprises at least one second conductive layer of material disposed upon the at least one of the at least one conductive layer of material which remains exposed and the at least one dielectric layer of material.

In another preferred embodiment, the electrode further comprises a lead attachment region. In one such embodiment, the at least one dielectric layer of material extends from the lead attachment region.

In another embodiment, the at least one conductive layer includes a proximal end and a distal end. The at least one dielectric layer extends substantially from the proximal end to the distal end of the at least one conductive layer.

In yet another preferred embodiment, the at least one dielectric layer of material is formed into a substantially contiguous herringbone pattern. In another preferred embodiment, the at least one dielectric layer of material comprises at least one strip. In one such embodiment, the at least one strip includes a distal end, the distal end is configured to include a taper, which, in turn, precludes concentrations of current therearound.

In another embodiment, the conductive layer of material further includes a proximal end and a distal end. In such an embodiment, the pattern comprises a pattern that is substantially symmetrical from the proximal to the distal end of the conductive layer of material about an axis bisecting the conductive layer of material.

In one embodiment, the electrode further includes a substrate associated with the first layer of material.

The invention further comprises an electrode, for use in an iontophoretic drug delivery apparatus, comprising a first conductive layer of material and at least one sacrificial layer of material disposed upon at least a portion of the at least one conductive layer of material.

In one embodiment, the first conductive layer is configured so as to substantially correspond to the dimensions of the at least one sacrificial layer of material. In another embodiment, the first conductive layer of material comprises a pattern. In yet another embodiment, the pattern comprises a plurality of intersecting strips of material. In another embodiment, the pattern comprises a herringbone pattern.

In a preferred embodiment, the electrode further comprises a transitional conductive material positioned between the conductive layer of material and the sacrificial layer of material.

In another preferred embodiment, the electrode further comprises a substrate associated with the conductive layer of material.

In another aspect of the invention, the invention comprises an electrode, for use in association with an iontophoretic drug delivery apparatus, comprising a conductive layer of material and means for substantially distributing current substantially uniformly about the conductive layer of material, upon supplying electrical current to the conductive layer of material.

In a preferred embodiment, the electrode comprises a positive electrode. In such an embodiment, the current distribution means comprises a dielectric layer of material disposed about at least a portion of, but less than the entirety, of the conductive layer of material.

In another such preferred embodiment, the electrode comprises a negative electrode. In such an embodiment, the current distribution means comprises a sacrificial layer of material disposed over at least a portion of the conductive layer of material.

The invention further comprises a method of manufacturing an electrode for use in association with an iontophoretic drug delivery apparatus. The method comprises the steps of providing a substrate; applying a conductive layer of material upon at least a portion of the substrate; and applying a dielectric layer of material upon a portion of, but less than the entirety of the conductive layer of materia.

In a preferred embodiment, the method further comprises the step of associating a lead to the conductive layer of material.

In one another preferred embodiment, the step of applying the dielectric layer comprises the step of extending the dielectric layer of material away from the lead.

In another preferred embodiment, the method further comprises the step of applying at least one conductive layer upon at least one of the exposed conductive layer of material and the dielectric layer of material.

In one embodiment, the step of applying a conductive layer of material comprises the step of printing the conductive layer of material upon the substrate. Similarly, the step of applying a dielectric layer of material may comprise the step of printing the dielectric layer of material upon the substrate.

The invention further comprises a method of manufacturing an electrode for use in association with an iontophoretic drug delivery apparatus. The method comprises the step of providing a substrate; applying a conductive layer of material upon a portion of the substrate; and applying a sacrificial layer of material upon the conductive layer of material.

In a preferred embodiment, the method further comprises the step of associating a lead to the conductive layer of material.

In another preferred embodiment, the method further comprises the step of applying a transition conductive layer after the step of applying a conductive layer of material.

The invention further comprises a method of uniformly distributing current along an electrode. The method comprises the steps of providing a conductive layer of material; associating a lead to the conductive layer of material; applying a dielectric layer of material to a portion of the conductive layer of material; extending away from the lead toward the extremities of the conductive layer of material; applying an electric current to the lead; and distributing the electric current along the conductive layer of material below the dielectric layer of material.

BEST MODE FOR PRACTICING THE INVENTION

While this invention is susceptible of embodiment in many different forms, there is shown in the drawings and will be described in detail, one specific embodiment with the understanding that the present disclosure is to be considered as an exemplification of the principles of the invention and is not intended to limit the invention to the embodiment illustrated.

Figure 1:
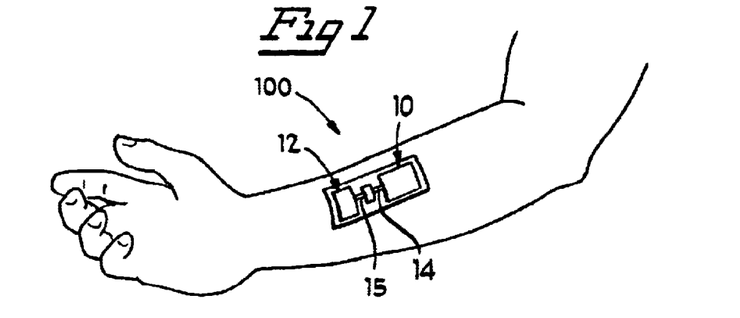
FIG. 1 of the drawings is a perspective view of an iontophoretic device having an electrode of the present invention.
Figure 2:
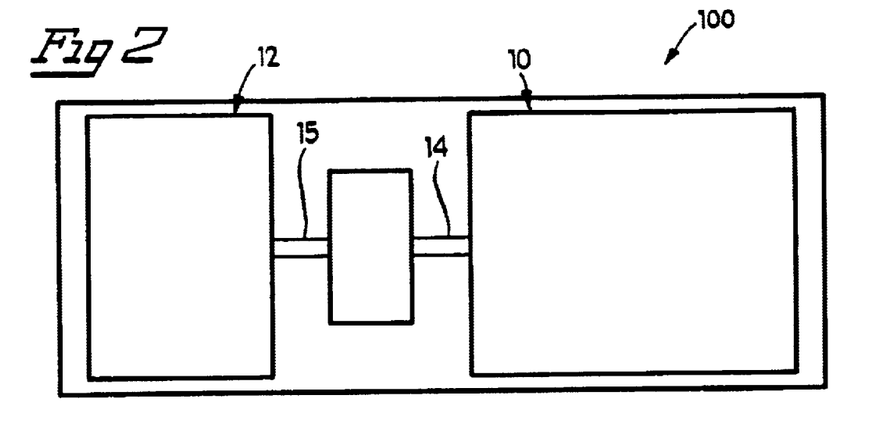
FIG. 2 of the drawings is a top plan view of one type of electrode assembly having electrodes of the present invention.

Referring to the Figures, and in particular FIGS. 1 and 2, iontophoretic delivery device is shown generally as 100. Such a device generally supplies an electric current to electrodes which are associated with a medicament. The electric current then drives the medicament through the skin of a patient. Device 100 generally includes a first electrode and a second electrode. In the embodiment shown in FIG. 2, the electrodes comprise positive electrode 10, negative electrode 12, and respective leads 14, 15 extending therefrom.

Figure 3:
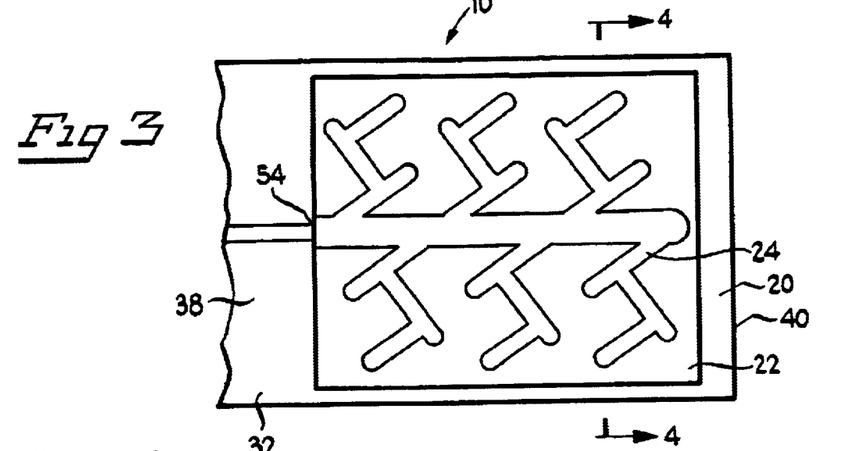
FIG. 3 of the drawings is a partial top plan view of the electrode assembly, showing in particular a first embodiment of a positive electrode made in accordance with the teachings of the present invention.
Figure 4:
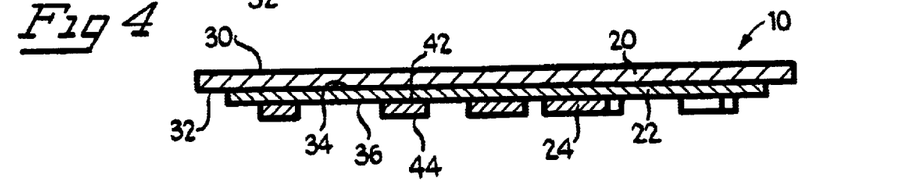
FIG. 4 of the drawings is a cross-sectional view of the embodiment of FIG. 3 taken generally about lines 4—4 of FIG. 3.

One embodiment of positive electrode 10 is shown in FIGS. 3 and 4 as comprising substrate 20, first conductive layer 22 and dielectric layer 24. Substrate 20 is shown in FIG. 4 as including upper surface 30 and lower surface 32. Generally substrate 20 comprises a polymer base web, such as a Mylar. Of course, other substrate materials, such as urethane, vinyl, paperboard, tyvec, gortex, plastic, glass as well as other flexible and/or rigid substrates of varying thicknesses are likewise contemplated for use. While the material is shown as being substantially planar, it is likewise contemplated that the material may comprise one which includes a shaped surface configured to match, for example, particular contours of body parts, or that the surface configuration may be undulating, so as to achieve a desired surface configuration.

First conductive layer 22 is shown in FIGS. 3 and 4 as comprising a layer of material which has electrically conductive properties. First conductive layer 22 further includes upper surface 34 (FIG. 3), lower surface 36 (FIG. 3), proximal end 38 (FIG. 4) and distal end 40 (FIG. 4). Upper surface 34 is associated with lower surface 32 of substrate 20. First conductive layer 22 may comprise a variety of materials. In one embodiment, first conductive layer 22 comprises silver/polymer based material which is formulated into an ink and printed upon the substrate. In such an embodiment, the silver layer may be 1 mil thick. In other embodiments, first conductive layer 22 may comprise silver foil, as well as other conductive materials suitable for use in association with the electrode. Lead 15 is associated with conductive layer 22 and is electrically connected to the first conductive layer by way of connection 54. In certain embodiments, lead 15 may be integral with conductive layer 22.

Dielectric layer of material 24 (also referred to sometimes as mask layer) is shown in FIGS. 3 and 4 as comprising upper surface 42 and lower surface 44. Upper surface 42 is positioned upon lower surface 36 of first conductive layer 22. The dielectric layer of material does not conduct electricity and, therefore, insulates a portion of the silver thereunder from participating in an electrical connection. The dielectric material may comprise a variety of materials, including but not limited to various polymers and other materials which are primarily insulative. Generally, the dielectric layer of material comprises a thickness of about 0.5–1 mil while other thicknesses are likewise contemplated for use.

Figure 7:
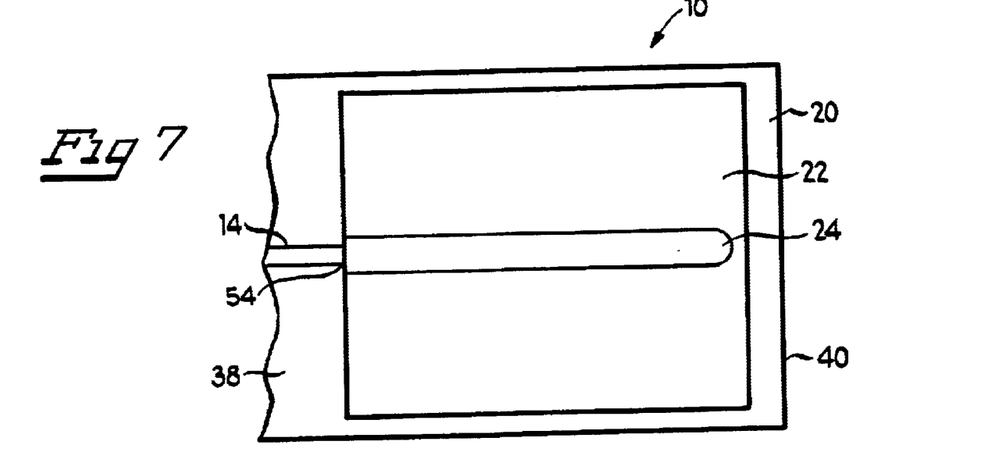
FIG. 7 of the drawings is a partial top plan view of the electrode assembly, showing in particular a third embodiment of a positive electrode made in accordance with the teachings of the present invention.
Figure 8:
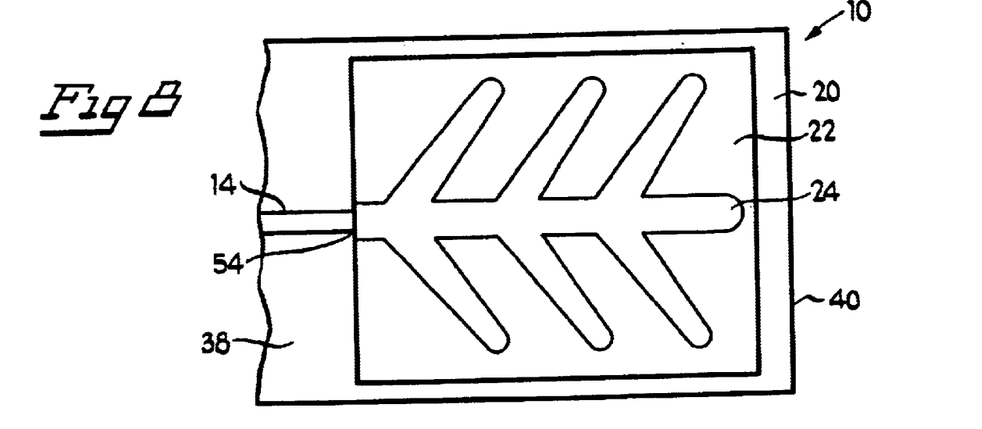
FIG. 8 of the drawings is a partial top plan view of the electrode assembly, showing in particular a fourth embodiment of a positive electrode made in accordance with the teachings of the present invention.
Figure 9:
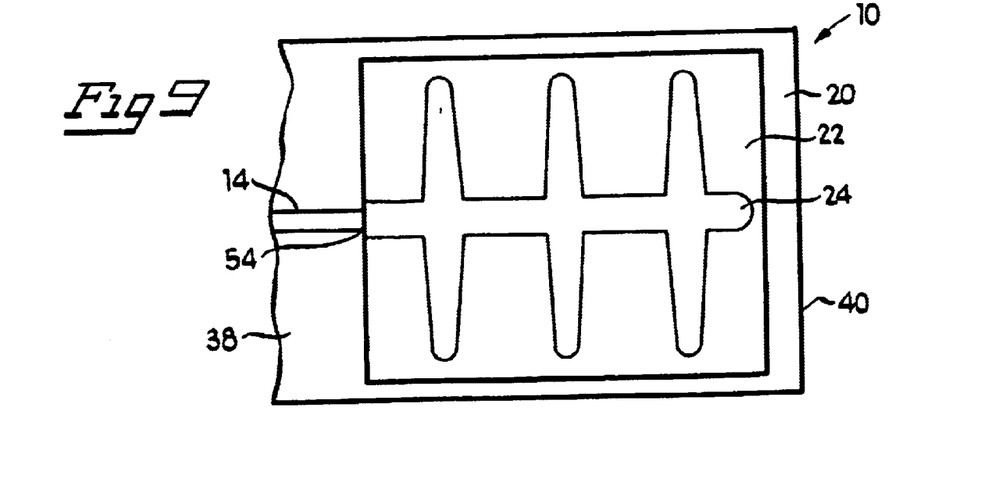
FIG. 9 of the drawings is a partial top plan view of the electrode assembly, showing in particular a fifth embodiment of a positive electrode made in accordance with the teachings of the present invention.

The dielectric layer of material may be formed into any number of shapes and configurations. In particular, and as shown in FIG. 7, the dielectric layer of material may be formed into a single strip that, for example, extends from the proximal end of the first conductive layer (proximate the lead) to the distal end of the first conductive layer. In other embodiments, as shown in FIG. 3, the dielectric layer of material may comprise a substantially contiguous pattern, such as a herringbone pattern. Of course other patterns are contemplated such as a branching pattern (FIG. 8), and a cris-cross pattern (FIG. 9), among others. Additionally, to preclude the concentration of current at the extremities of the dielectric material (i.e. the regions which are distally positioned relative to the lead), such extremities may be tapered. Indeed, the invention is not limited to any particular shape, and, different shapes may become rather useful in certain embodiments and in certain fields of use.

Figure 5:
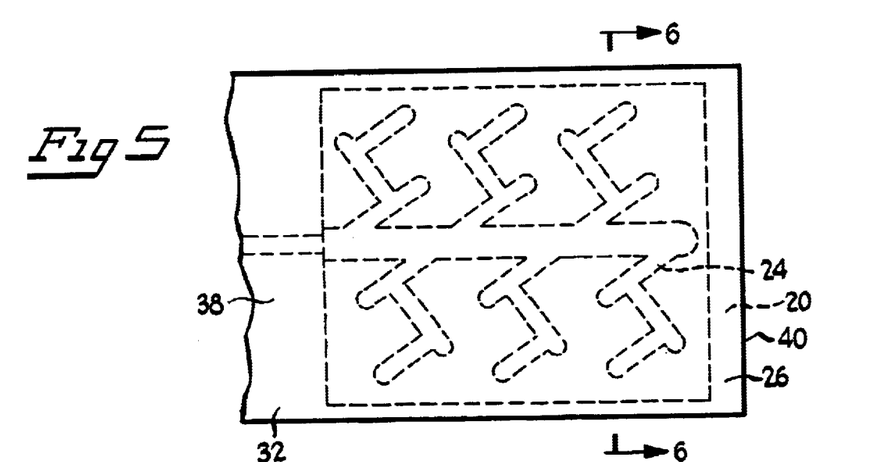
FIG. 5 of the drawings is a partial top plan view of the electrode assembly, showing in particular a second embodiment of a positive electrode made in accordance with the teachings of the present invention.
Figure 6:
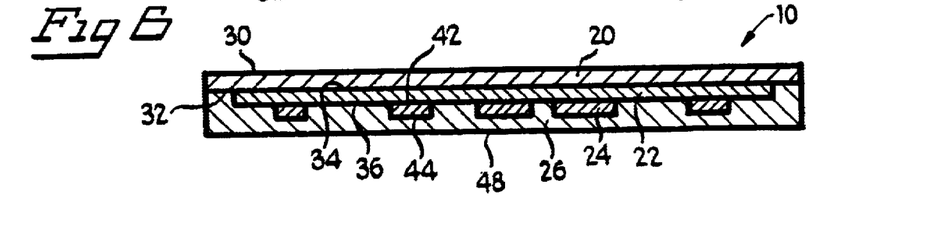
FIG. 6 of the drawings is a cross-sectional view of the embodiment of FIG. 5 taken generally about lines 6—6 of FIG. 5.

In certain embodiments, as shown in particular in FIGS. 5 and 6, the electrode may further include at least one second conductive layer, such as second conductive layer 26 (FIG. 6). As shown in FIG. 6, each such layer includes upper surface 46 and lower surface 48. Upper surface 46 is applied to and associated with lower surface 44 of dielectric layer of material 24, and lower surface 36 of conductive layer of material 22 (where the first conductive layer of material is not covered by the dielectric layer of material). While not required, such a layer may include multiple second layers of material. Second conductive layer of material 26 generally comprises a material similar to (and often identical to) first conductive layer of material 22. Such a material may be applied in a manner similar to that of first conductive layer of material, and may comprise a thickness similar to that of the first conductive layer of material (several applications of a second conductive layer of material serve to increase the overall thickness of the conductive material).

To manufacture the above-described electrode, substrate 20 is provided. Once provided, the substrate is cut to the desired dimensions. Next, first conductive layer 22 is applied thereto. In particular, the first conductive layer can comprise an ink which is silkscreened upon the substrate. In other embodiments, the first conductive layer may be pad printed, jet ink printed, flexigraphically applied to the substrate. Indeed, the apparatus is not limited to any particular method of application of the first conductive layer.

Once the first conductive layer of material is applied, the lead is associated with the first conductive layer. In the embodiment shown, lead 14 is integrated with the first conductive layer of material, and, in turn, applied together with the first conductive layer of material upon the substrate.

Next, a dielectric material is supplied and configured to a desired pattern or configuration. Once configured, the dielectric material is applied to the first conductive layer of material. In particular, the dielectric may comprise a tape or adhesive layer, or, a printed layer (which may be, for example, UV curable). In the embodiments illustrated, the dielectric layer may cover only particular regions of the first conductive layer, and the invention is not limited to any particular shapes or configurations.

In certain embodiments, additional conductive layers of material may be positioned upon the electrode (i.e. over the dielectric layer of material and the exposed first conductive layer of material). Such layers of material provide further material for the chemical reaction that takes place in operation of the electrode.

Figure 11:
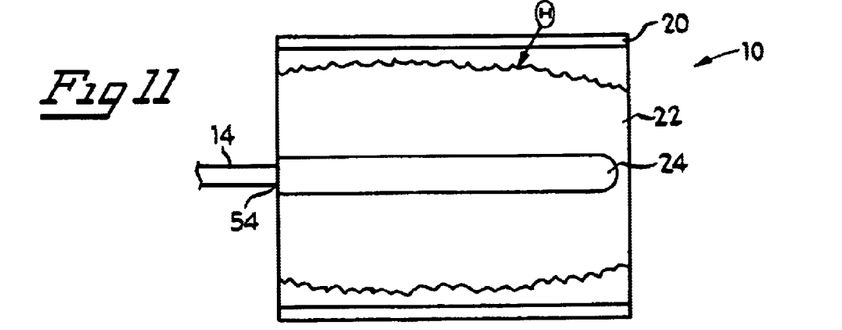
FIG. 11 of the drawings is a schematic partial top plan view of the positive electrode assembly, showing in particular the current distribution across the surface of the electrode.

In operation, as a current is applied to the lead, the current extends to the first layer of material. The portion of the first layer of material that is exposed begins to undergo a reaction (in the Ag/AgCl example, the silver reacts with chlorine to become silver chloride). However, the region immediately below the masked portions is substantially precluded from participating in the reaction, and, as a result provides a substantially pristine pathway for the current. In turn, the current becomes substantially uniformly distributed about the electrode (or the desired regions of the electrode). As can be seen by a comparison of the current distribution of a prior art electrode in FIG. 10 (denoted by Θ) and the current distribution of an electrode of the present invention in FIG. 11 (denoted by Θ), it is clear that the current is substantially more evenly distributed in the electrode of FIG. 11 as compared to the electrode of FIG. 10.

Figure 12:
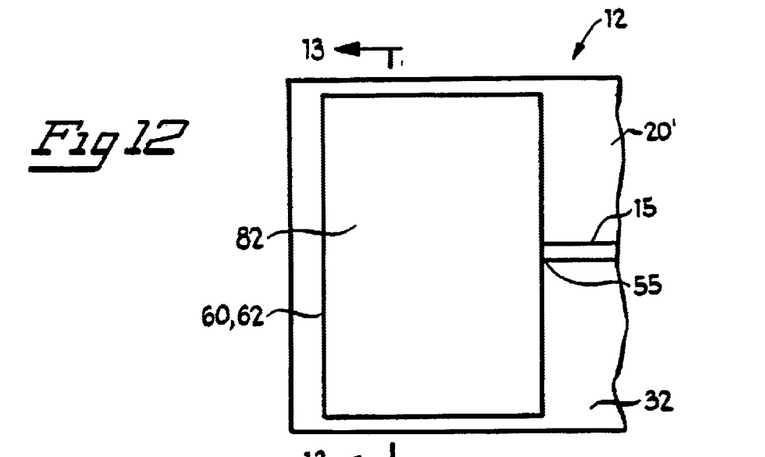
FIG. 12 of the drawings is a partial top plan view of the electrode assembly, showing in particular a first embodiment of a negative electrode made in accordance with the teachings of the present invention.
Figure 13:
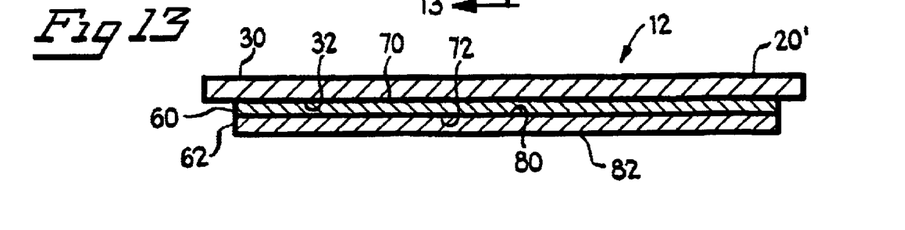
FIG. 13 of the drawings is a cross-sectional view of the embodiment of FIG. 12 taken generally about lines 13—13 of FIG. 12.

A similar structure can be seen relative to negative electrode 12. In particular, as shown in FIGS. 12 and 13. In particular, negative electrode 12 includes substrate 20', conductive layer 60 and sacrificial layer 62. While not required, in the embodiment shown in FIG. 1, the substrate for the negative and the positive electrodes may comprise a single piece of material, as such substrate 20' includes upper surface 30 and lower surface 32. Of course, in other embodiments, the two electrodes can be separated, and, the substrates for each may be distinct and separate components.

Figure 14:
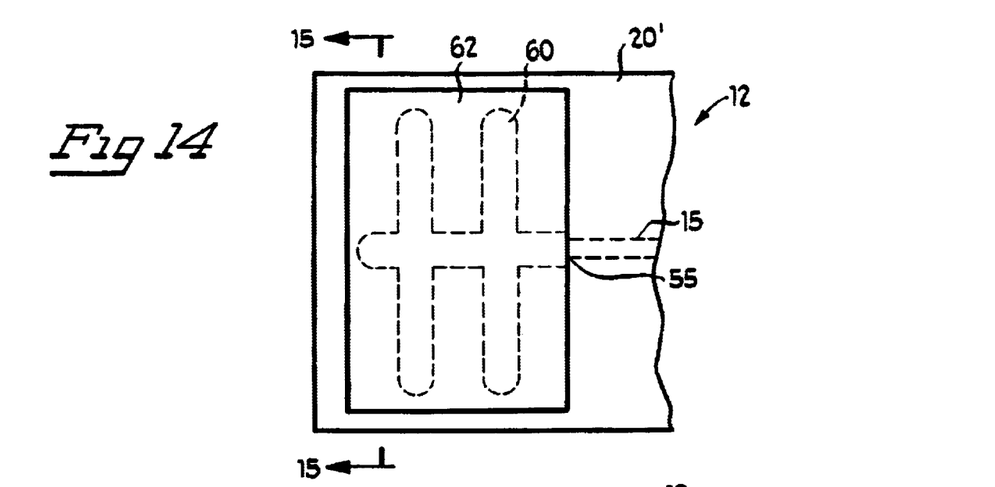
FIG. 14 of the drawings is a partial top plan view of the electrode assembly, showing in particular a second embodiment of a negative electrode made in accordance with the teachings of the present invention.
Figure 15:
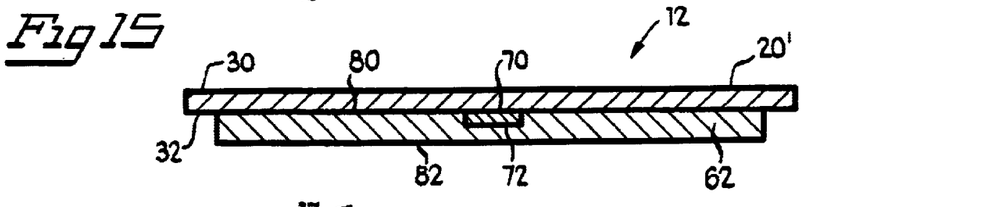
FIG. 15 of the drawings is a cross-sectional view of the embodiment of FIG. 14 taken generally about lines 15—15 of FIG. 14.

Referring now to FIG. 13, conductive layer 60 is positioned upon lower surface 32 of substrate 20'. The conductive layer includes upper surface 70 and lower surface 72, and, may comprise a highly conductive material, such as silver, aluminum, as well as other metals and alloys thereof, along with various other conductive materials, such as carbon based materials. The conductive layer may comprise a single layer of uniform thickness and uniform cross-section (FIG. 13). In other embodiments, the conductive layer may comprise a particular pattern (FIG. 14).

Sacrificial layer 62, as shown in FIG. 13, is positioned upon lower surface 72 of conductive layer 60, and includes upper surface 80 and lower surface 82. Sacrificial layer 62 has a level of conductivity (generally lower than that of conductive layer 60). Certain particles of the sacrificial layer undergo a chemical reaction. For example, wherein the sacrificial material comprises a combination of silver and silver chloride, in operation, the chloride is separated from the silver so as to form chloride ions and silver. As such, the sacrificial material, upon completion of its use, has substantially reacted such that it comprises primarily silver (and very little silver chloride). Of course, in other embodiments, the sacrificial layer may comprise various different materials.

Figures 16, 17:
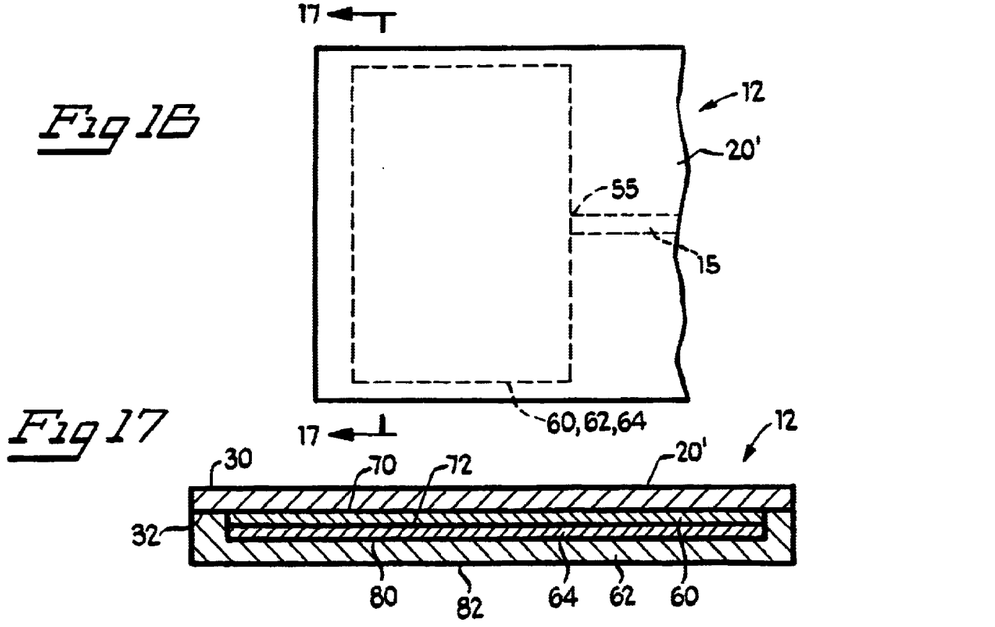
FIG. 16 of the drawings is a partial top plan view of the electrode assembly, showing in particular a third embodiment of a negative electrode made in accordance with the teachings of the present invention.
FIG. 17 of the drawings is a cross-sectional view of the embodiment of FIG. 16 taken generally about lines 17—17 of FIG. 16.

As shown in the embodiment of FIGS. 16 and 17, it may be necessary to include a transition conductive layer 64 between conductive layer 60 and sacrificial layer 62. Transition conductive layer 64 is useful wherein conductive layer 60 and sacrificial layer 62 are generally not compatible. One such example is wherein conductive layer 60 comprises, for example, aluminum, and sacrificial layer 62 comprises sliver/sliver chloride These two materials are highly reactive, and exposure of aluminum to the silver/silver chloride will corrode the aluminum. In such an embodiment, a conductive silicon-rubber (i.e. carbon) based material may be inserted between the aluminum and the silver/silver chloride to preclude direct contact of the two reactive materials.

To assemble the negative electrode of FIGS. 12 and 13, a substrate is provided. As explained above, the substrate of each of the positive and negative electrode may be unitized. Once provided, a conductive layer of material is disposed thereon. In one embodiment, the conductive layer of material may comprise a printed ink, a film, a paintable coating, etc. Of course other methods of applying a conductive layer upon a substrate are contemplated for use. As explained above, the layer may be applied as a uniform layer, or the layer may comprise a pattern or a particular configuration. The invention is not limited to any particular configuration of the conductive layer of material. Regardless of the configuration, once applied, lead 14 may be associated with the conductive layer of material. Indeed, as with the positive electrode, the respective lead may be integrated with the conductive layer of material.

Next, sacrificial layer of material 62 is applied to the conductive layer of material (and to exposed portions of the substrate wherein the application of the conductive material is, for example, patterned). Such a layer may likewise comprise the printing of a sacrificial ink upon the surface, or the layer may be applied in any of the above-identified manners relative to the other layers.

In the embodiment of FIGS. 16 and 17, it may become necessary to apply a transitional conductive layer. In such an embodiment, the transitional conductive layer is applied to the conductive layer of material prior to the application of the sacrificial layer of material.

Figure 19:
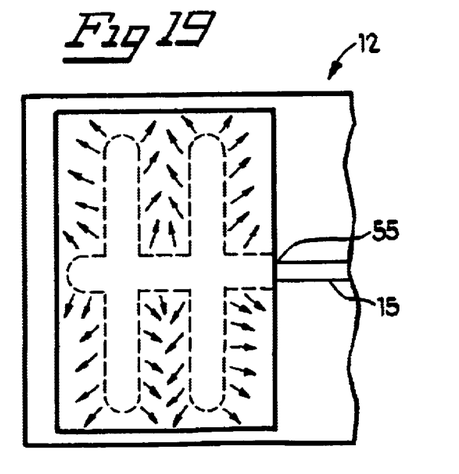
FIG. 19 of the drawings is a schematic partial top plan view of the negative electrode assembly, showing in particular the current distribution across the surface of the electrode.

In operation, as the current is applied to the electrode, as shown in FIG. 19, the current will spread substantially uniformly across the surface of the electrode via the conductive layer of material. As such, the reaction can proceed more uniformly across the entire electrode, rather than (as shown relative to prior art devices in FIG. 18), extending as a front across the electrode over a period of time.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An electrode, for use in an iontophoretic drug delivery apparatus, comprising:
   at least one first conductive layer of material having a proximal end, a distal end, and an axis extending between the proximal and distal end, wherein the conductive layer undergoes an electrochemical reaction upon application of an electric current, the conductive layer having at least one lead attachment region associated with the proximal end; and
   at least one dielectric layer of material disposed upon at least a portion of, but less than the entirety of, the at least one conductive layer of material, wherein the dielectric layer is configured in a continuous and uninterrupted pattern extending from the at least one lead attachment region to a region of the conductive layer distally spaced from the lead attachment region, the pattern comprising a substantially linear trunk running along the axis of the conductive layer, having at least one terminal end.

2. The electrode of claim 1 further comprising at least one second conductive layer of material disposed upon the at least one of the at least one conductive layer of material which remains exposed and the at least one dielectric layer of material.

3. The electrode of claim 1 wherein the pattern is formed into a substantially contiguous herringbone pattern.

4. The electrode of claim 1 wherein the pattern comprises at least one strip.

5. The electrode of claim 4 wherein the at least one terminal end is configured to include a taper, to, in turn, preclude concentrations of current therearound.

6. The electrode of claim 1 wherein the pattern is substantially symmetrical from the proximal to the distal end of the conductive layer of material about the axis, wherein the axis bisects the conductive layer of material.

7. The electrode of claim 1 further including a substrate associated with the first layer of material.

8. The electrode of claim 1, wherein the pattern further comprises at least one branch.

9. An electrode, for use in an iontophoretic drug delivery apparatus, comprising:
   a first conductive layer of material, which does not undergo a chemical reaction upon application of an electrical current, the first conductive layer having at least one lead attachment region; and
   at least one sacrificial layer of material disposed upon at least a portion of the at least one conductive layer of material and having a proximal end, a distal end, and an axis extending between the proximal and distal end, wherein the lead attachment region of the first conductive layer is associated with the proximal end;
   wherein the first conductive layer of material is configured in a continuous and uninterrupted pattern extending from the at least one lead attachment region to a region of the at least one sacrificial layer of material proximate the distal end, wherein the pattern comprises a substantially linear trunk running along the axis of the sacrificial layer, having at least one terminal end.

10. The electrode of claim 9 wherein the first conductive layer is configured so as to substantially correspond to the dimensions of the at least one sacrificial layer of material.

11. The electrode of claim 9 wherein the pattern comprises a plurality of intersecting strips of material.

12. The electrode of claim 9 wherein the pattern comprises a herringbone pattern.

13. The electrode of claim 9 further comprising a transitional conductive material positioned between the conductive layer of material and the sacrificial layer of material.

14. The electrode of claim 9 further comprising a substrate associated with the conductive layer of material.

15. The electrode of claim 9, wherein the pattern further comprises at least one branch.

16. A method of manufacturing an electrode for use in association with an iontophoretic drug delivery apparatus comprising the steps of:
  providing a substrate;
  applying a conductive layer of material upon at least a portion of the substrate, the conductive layer having a proximal end, a distal end, and an axis extending between the proximal and distal end, wherein the conductive layer undergoes an electrochemical reaction upon application of an electric current, the conductive layer having at least one lead attachment region associated with the proximal end; and
  applying a dielectric layer of material upon a portion of, but less than the entirety of the conductive layer of material, wherein the dielectric layer is configured in a continuous and uninterrupted pattern extending from the at least one lead attachment region along the axis of the conductive layer to a region of the conductive layer proximate the distal end, the pattern comprising a substantially linear trunk running along the axis of the conductive layer, and having at least one terminal end.

17. The method of claim 16 further comprising the step of:
  associating a lead with the at least one attachment region.

18. The method of claim 16 further comprising the step of:
  applying at least one conductive layer upon at least one of the exposed conductive layer of material and the dielectric layer of material.

19. The method of claim 16 wherein the step of applying a conductive layer of material comprises the step of:
  printing the conductive layer of material upon the substrate.

20. The method of claim 16 wherein the step of applying a dielectric layer of material comprises the step of:
  printing the dielectric layer of material upon the substrate.

21. The method of claim 15, wherein the pattern further comprises at least one branch.

22. A method of manufacturing an electrode for use in association with an iontophoretic drug delivery apparatus comprising the step of:
  providing a substrate;
  applying a conductive layer of material upon a portion of the substrate, which does not undergo a chemical reaction upon application of an electric current, the conductive layer having at least one lead attachment region; and
  applying a sacrificial layer of material upon the conductive layer of material, the sacrificial layer having a proximal end, a distal end, and an axis extending between the proximal and distal end, wherein the lead attachment region is associated with the proximal end;
  wherein the first conductive layer of material is applied to the substrate in a continuous and uninterrupted pattern extending from the at least one lead attachment region along the axis of the sacrificial layer to a region of the at least one sacrificial layer proximate the distal end of the sacrificial layer, wherein the pattern comprises a substantially linear trunk running along the axis of the sacrificial layer, and having at least one terminal end.

23. The method of claim 22 wherein the step of applying a conductive layer comprises the step of:
  printing the conductive layer of material upon the substrate.

24. The method of claim 22 wherein the step of applying a sacrificial layer of material comprises the step of:
  printing the sacrificial layer of material upon at least a portion of the conductive layer.

25. The method of claim 22 further comprising the step of:
  applying a transition conductive layer after the step of applying a conductive layer of material.

26. The method of claim 22, wherein the pattern further comprises at least one branch.

* * * * *